United States Patent [19]

Lysenko

[11] Patent Number: 5,567,843
[45] Date of Patent: Oct. 22, 1996

[54] PROCESS FOR MAKING 2-ARYL BENZ (OX, THI, IMID)AZOLES AND 2-AMINOARYL AMINOBENZ(OX, THI, IMID)AZOLES

[75] Inventor: Zenon Lysenko, Midland, Mich.

[73] Assignee: The Dow Chemical Company, Midland, Mich.

[21] Appl. No.: 407,349

[22] Filed: Mar. 20, 1995

[51] Int. Cl.$^6$ .................. C07B 43/02; C07D 263/57; C07D 235/18; C07D 277/66

[52] U.S. Cl. .................. 562/804; 548/224; 548/310.7; 548/178; 564/419

[58] Field of Search .................. 562/804; 548/224, 548/310.7, 178; 564/419

[56] References Cited

U.S. PATENT DOCUMENTS

| | | | |
|---|---|---|---|
| 4,087,409 | 5/1978 | Preston | 260/65 |
| 4,831,193 | 5/1989 | Lamendola et al. | 564/417 |
| 4,880,926 | 11/1989 | Fujiwara et al. | 544/105 |
| 5,017,280 | 5/1991 | Paris-Marcano | 208/223 |
| 5,223,617 | 6/1993 | Hammond et al. | 544/190 |

OTHER PUBLICATIONS

Dondoui, et al., Synthesis (1987), 11, 998–1001.
Tsuge, et al., Chem. Lett., (1986) 183–186.
Tsuge, et al., Bull. Chem. Soc. Jpn., (1987), 60, 2463–73.
Abdelhamid et al., "Synthesis of Fused Ring Heterocycles from Aromatic Amines with Hydroximoyl Chlorides," *J. Heterocyclic Chem.*, 25, 1988, pp. 403–405.

*Primary Examiner*—Johann Richter
*Assistant Examiner*—Laura R. Cross

[57] ABSTRACT

2-(aryl)-benz(ox, thi, imid)azoles are prepared by reacting an aromatic aldehyde with hydroxylamine to form an aromatic aldehyde oxime, halogenating the oxime to form an aromatic hydroxamoyl halide, and then reacting this halide with certain aromatic amine compounds. The products may be nitrated and then reduced to form the corresponding diamines, which are useful in making PIBX polymers.

11 Claims, No Drawings

PROCESS FOR MAKING 2-ARYL BENZ (OX, THI, IMID)AZOLES AND 2-AMINOARYL AMINOBENZ(OX, THI, IMID)AZOLES

BACKGROUND OF THE INVENTION

This invention relates to a process for making 2-aryl benz(ox, thi, imid)azoles and 2-aminoaryl amino-benz(ox, thi, imid)azoles. The term "benz(ox, thi, imid)azole" is used herein as a shorthand term to designate an oxazole, thiazole or imidazole group which is fused to an aromatic ring at the 4 and 5 positions.

Polyimide benz(ox, thi, imid)azole (PIBX) polymers can be prepared by reacting a dianhydride with a diamine containing one or more benz(ox, thi, imid)-azole groups. See, for example U.S. Pat. No. 4,087,409 to Preston, incorporated herein by reference. Among the useful benz(ox, thi, imid)azole-containing diamines are those in which the 2 position of the oxazole ring is substituted with an aminoaryl group. Among the diamines of the latter type are those represented by the structure:

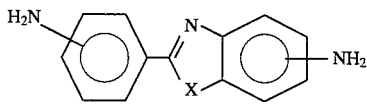

wherein X is —O—, —S—, or —NH—.

These latter amines can be prepared by reacting an amino benzoic acid with 2,4- or 2,5-diamino phenol, 2,4- or 2,5-diamino phenyl mercaptan, or 1,2,4- triaminobenzene (when X is —O—, —S—, and —NH—, respectively). For example, it is known to prepare 2-(m-aminophenyl)-aminobenzoxazole (DAMBO) by reacting 2,4-diaminophenol with meta- or para-aminobenzoic acid in the presence of polyphosphoric acid. Unfortunately, however, this process suffers from several drawbacks. The reaction mixture requires extensive neutralization, and thus forms large volumes of aqueous phosphate salts as a waste stream. The product must be purified extensively through repeated sublimations in order to be useful as a monomer. In addition, the diaminophenol and aminobenzoic acid starting materials are expensive and not readily available.

For these reasons, it would be desirable to provide an alternate method for making DAMBO as well as other 2-aminoaryl aminobenz(ox, thi, imid)azoles.

SUMMARY OF THE INVENTION

In one aspect, this invention is a process for preparing a 2-(aryl)-benz(ox, thi, imid)azole, comprising:

(a) contacting an aromatic aldehyde with hydroxylamine under conditions such that an aromatic aldehyde oxime is formed;

(b) contacting said aromatic aldehyde oxime with a halogenating agent under conditions such that an aromatic hydroxamoyl halide is formed; and (c) contacting the aromatic hydroxamoyl halide with an aromatic amine compound which has a primary amine group ortho to a hydroxyl group, a thiol group or another primary amine group to form a 2-(aryl)-benz(ox, thi, imid)azole.

In this process, both the aromatic aidehyde and the aromatic amine compound may be nitro-substituted. In such case, the nitro group or groups may be reduced to primary amine groups after step (c). In the case where neither, or only one of the aromatic aldehyde and the aromatic amine compound is nitro-substituted, the benz(ox, thi, imid)azole may be nitrated after step (c) so that following the nitration, both the benz(ox, thi, imid)azole and the aromatic substituent at the 2-position contain a nitro group. These nitro groups may be then reduced to amines.

Steps (a), (b), and (c) can be performed under mild conditions to obtain high yields of benz(ox, thi, imid)azole at essentially 100% selectivity, and do not require the use of polyphosphoric acid. Moreover, the process of this invention makes use of relatively inexpensive starting materials.

DETAILED DESCRIPTION OF THE INVENTION

In the first step of this process, an aromatic aldehyde is contacted with hydroxylamine under conditions such that an aromatic aldehyde oxime is formed. By "aromatic aldehyde", it is meant a compound in which a group represented by the structure:

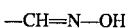

is bonded directly to an aromatic nucleus of an aromatic ring structure.

The aromatic aldehyde is a compound having a —CHO group directly bonded to an aromatic nucleus of an aromatic ring structure. Suitable aromatic ring structures to which the —CHO group is bonded include pyridine, benzene and fused ring systems such as anthracene, naphthalene and the like. The aromatic ring structure may be unsubstituted or substituted. However, any substituted ring structure must contain either a hydrogen or a nitro group attached to an aromatic nucleus, or else at least one of the substituent groups must be capable of being replaced by a nitro group after the benz(ox, thi, imid)azole is formed. In addition, any substituent group should not react under the conditions of the reaction with hydroxylamine with the aromatic aidehyde, or of the subsequent reactions with a halogenating agent and with the aromatic amine compound. Suitable substituents include phenyl, phenoxyl, —SO₂—(C₆H₅) and the like. It is preferred, but not necessary, that the aromatic aldehyde contain a nitro group bonded to an aromatic ring. Benzaldehyde and mononitrobenzaldehyde are preferred aromatic aldehydes, with m- and p-nitrobenzaldehyde being especially preferred.

The hydroxylamine (H₂NOH) may be and preferably is used in the form of a salt of a protic acid, such as the HCl salt. The hydroxylamine is preferably used in a slight excess relative to the aromatic aldehyde.

The aromatic aldehyde and the hydroxylamine are advantageously contacted in the presence of a solvent or diluent. Preferred solvents are polar materials in which both the aldehyde and the hydroxylamine are soluble. Alternatively, nonsolvents can be used as diluents. It is also preferred that the solvent be one which boils within the preferred or more preferred temperature range described below, so the reaction may be conducted under refluxing conditions. Suitable solvents include, for example, ethanol, methanol, isopropanol, 1,4-dioxane, tetrahydrofuran, and polar aprotic solvents that are inert to the reactants and the products, as well as toluene and benzene.

The reaction is preferably conducted at an elevated temperature at which the aromatic aldehyde does not degrade. A preferred temperature is from about 30° to about 120° C., with a temperature from about 50° to about 95° C. being more preferred. At the more preferred temperature, a reaction time of from about ½ hour to about 8 hours is generally sufficient to essentially complete the reaction.

The resulting aromatic aldehyde oxime is then reacted with a halogenating agent under oxidizing conditions to form the corresponding aromatic hydroxamoyl halide. By "aromatic hydroxamoyl halide", it is meant a compound in which a group represented by the structure:

is bonded directly to a nucleus of an aromatic ring structure. In the foregoing structure, A represents a halogen atom, preferably chlorine or bromine.

The halogenation proceeds well even under mild conditions, and for that reason it is preferable to use mild halogenating agents and conditions in order to avoid halogenation at other sites on the aromatic aldehyde oxime molecule. Suitable halogenating agents include chlorine ($Cl_2$), bromine ($Br_2$), hypochlorous acid (HOCl), hypobromous acid, and materials which generate hypochlorous or hypobromous acid in situ. Chlorine, bromine, hypochlorous acid and hypobromous acid are advantageously used as dilute solutions, preferably as aqueous solutions. Materials which produce hypochlorous acid in situ include, for example, aqueous mixtures of sodium hypochlorite and a mineral acid, especially HCl; mixtures of a peroxysulfate salt such as potassium peroxysulfate with HCl; and mixtures of N-chlorosuccinamide with aqueous HCl. In analogous fashion, hypobromous acid may be formed in situ from aqueous mixtures of sodium hypobromite and a mineral acid, mixtures of a peroxysulfate salt such as potassium peroxysulfate with HBr; and a mixture of N-bromosuccinamide with aqueous HCl. In preferred embodiments, the halogenating agent is a mixture of bleach (sodium hypochlorite solution) with a mineral acid, especially HCl, or an aqueous mixture of a peroxysulfate salt with HCl or HBr. In any of these preferred embodiments, HCl or HBr may be used in the form of an HCl or HBr salt of N,N-dimethylformamide.

The halogenating agent is advantageously used in at least a stoichiometric amount, and preferably in slight excess, based on the aromatic aldehyde oxime.

The halogenation reaction may be conducted in the presence of a solvent or diluent. The solvents which are useful for the reaction between the aromatic aldehyde and the hydroxylamine are generally useful in this step as well.

A suitable temperature for the halogenation step is from about −30° to about 100° C. preferably from about −10° to about 40° C.

The resulting aromatic hydroxamoyl halide is then reacted with an aromatic amine compound having a primary amine group ortho to a hydroxyl group, a thiol group, or another primary amino group. In this manner an oxazole, thiazol or imidazole is formed in which an aromatic ring structure corresponding to that of the aromatic hydroxamoyl halide is bonded to the 2-position. The oxazole, thiazole or imidazole group is formed when the aromatic amine compound contains a hydroxyl, thiol or another primary amine group, respectively, ortho to a primary amine group.

The aromatic amine contains an aromatic ring structure which may be monocyclic or polycyclic. The aromatic ring structure may contain substituents other than those mentioned before (i.e., the primary amine group and the hydroxyl, thiol or second primary amine group ortho to the primary amine group). However, any substituted ring structure must contain either a hydrogen or a nitro group attached to an aromatic nucleus, or else at least one of the substituent groups must be capable of being replaced by a nitro group after the benz(ox, thi,imid)azole is formed. Further, any substituent group should not react under the conditions of the reaction with the aromatic hydroxamoyl halide to form the benz(ox, thi, imid)azole. Preferred aromatic amine compounds include those in which the aromatic ring structure is pyridine, benzene, anthracene, naphthalene, nitropyridine, nitrobenzene, nitroanthracene, nitronaphthalene and the like, of which benzene and nitrobenzene are more preferred.

The reaction to form the benz(ox, thi, imid)azole can be conducted by mixing the reactants with heating to a temperature from about 20° to about 150° C. It is advantageous to use a solvent, with those which boil in the stated temperature range being preferred. Among the suitable solvents are methyl ethyl ketone, 1,4-dioxane, toluene and chlorobenzene. It is preferred to use the aromatic amine compound and the aromatic hydroxamoyl halide in a mole ratio from about 0.5:1 to 1:0.5, more preferably from about 0.7:1 to 1:0.7.

The resulting benz(ox, thi, imid)azole has an aromatic ring structure corresponding to that of the aromatic amine compound fused to the 4 and 5 positions of the benz(ox, thi, imid)azole ring. At the 2 position of the benz(ox, thi, imid)azole ring there is another aromatic ring structure corresponding to that of the aromatic hydroxamoyl halide.

If both of the aromatic ring structures of the benz(ox, thi, imid)azole contain a nitro group, a 2-aminoaryl-aminobenz (ox, thi, imid)azole is prepared by reducing the nitro groups to amine groups. Any method may be used to accomplish this reduction provided that it selectively reduces the nitro groups and does not hydrogenate the aromatic rings (including the (ox, thi, imid)azole ring). One suitable method is to contact the benz(ox, thi, imid)azole with hydrogen or other hydrogenating agent in the presence of a metal catalyst. Suitable metal catalysts include platinum and palladium, organometallic complexes of cobalt, nickel, titanium, zirconium and hafnium. The catalyst may be and preferably is supported on a porous support. Platinum and palladium are preferred catalysts, with platinum on carbon and palladium on carbon being particularly preferred. The amount of catalyst is chosen to provide an acceptable reaction rate, and typically is (but is not limited to) from about 1 part by weight catalyst per 5 to 5000 parts of the benz(ox, thi, imid)azole to be hydrogenated. It will be understood that many methods for conducting this hydrogenation may be used, and the selection of a particular method is not generally critical to this invention.

In the preferred hydrogenation method, the benz(ox, thi, imid)azole is contacted with hydrogen at a partial pressure of from about 0 to about 5000 psig, at any temperature at which an adequate reaction rate is achieved, preferably from about 25° C. to about 100° C.

When one or both of the aromatic ring structures of the benz(ox, thi, imid)azole lacks a nitro group, it is necessary to nitrate the benz(ox, thi, imid)azole before the reduction is done. The method by which the nitration is accomplished is not critical provided that undesired side reactions do not occur. Accordingly, the known methods for accomplishing ring nitration of aromatic compounds can be used. A preferred method is to contact the benz(ox, thi, imid)azole with nitric acid in the presence of sulfuric acid, preferably at a temperature range of from about 0° C. to about 25° C. using conditions that prevent multiple nitrations of either aromatic ring structure. It is preferred that, following any nitration, each aromatic ring structure contains only one nitro group. Once the needed nitro group or groups are added, they are hydrogenated to the corresponding primary amine as described before.

The resulting 2-(aminoaryl)-amino benz(ox, thi, imid)azole may be recovered from the reaction mixture by filtering out the catalyst and removing the solvent.

The 2-(aminoaryl)-amino benz ( ox, thi, imid)azole can be used to make PIBX (polyimidebenzoxazole or polyimidebenzthiazole) polymers by reaction with an aromatic dianhydride, as described in the copending application of Hwang et al. entitled POLYAMIC ACIDS AND METHODS TO CONVERT POLYAMIC ACIDS INTO POLYIMIDEBENZOXAZOLE FILMS, Ser. No. 331,755, filed Oct. 31, 1994. This reaction is typically conducted in two stages. In the first stage, the 2-(aminoaryl)-aminobenz(ox, thi, imid)azole and the dianhydride are reacted to form a polyamic acid. This is readily accomplished by contacting the dianhydride and the 2-(aminoaryl)-aminobenz(ox, thi, imid)azole at a temperature from about −20° C. to about 100° C. in a polar solvent. The resulting polyamic acid may then be converted to the PIBX by condensing some or all of the amic acid linkages. This is conveniently accomplished by heating the polyamic acid to an elevated temperature which may range up to about 600° C., but is preferably about 160° to about 280° C. Alternatively, a ring-closure agent such as acetic anhydride, proprionic anhydride, ketene or isobutyric dianhydride or salts thereof may be contacted with the polyamic acid to promote formation of imide rings. Following the imidization reaction, it is preferred to further heat the PIBX to a temperature from about 300° to about 600° C., which improves tensile properties of the polymer.

The PIBX polymer can be used to make films, fibers or other shaped articles. Such articles are conveniently prepared by forming a solution of the PIBO in a suitable solvent and extruding, coating, casting or spraying the solution. Preferably, however, such articles are prepared from the polyamic acid solution, which is imidized after the shaped article is formed.

The following examples are provided to illustrate the invention, but are not intended to limit the scope thereof. All parts and percentages are by weight unless otherwise indicated.

EXAMPLE 1

In a 1-liter flask equipped with a reflux condenser and a stirrer is charged 75 grams (0.5 moles) of 4-nitrobenzaldehyde, 500 milliliters of 1,4-dioxane and 38 grams (0.55 moles) of hydroxylamine hydrochloride. The mixture is heated to reflux with stirring for five hours, and then filtered. The reaction proceeds essentially quantitatively to form a solution containing approximately 0.5 mole of 4nitrobenzaldoxime.

The resulting 4-nitrobenzaldoxime solution is added to 400 additional milliliters of 1,4-dioxane, 100 milliliters of dimethylformamide which is saturated with 20 grams (0.55 mole) of HCl, and 338 grams (0.55 moles) of a potassium peroxysulfate solution sold by DuPont under the trade designation Oxone. The resulting mixture is stirred for about 18 hours, using an ice bath to control the exotherm to below 40° C. An additional 5 grams of HCl (dissolved in 50 milliliters of dimethylformamide) is then added, and the mixture stirred for an additional 5 hours. The mixture is then washed with acetic acid and water, and 4-nitrophenylchloroxime (4-nitrophenyl hydroxamoyl chloride) is recovered.

About 60 grams (0.3 mole) of the 4-nitro-phenylchloroxime is mixed with 340 milliliters of ethanol, 60 grams (0.39 moles) of 2-amino-4-nitrophenol and 60 milliliters of dimethylformamide. The mixture is heated to reflux for about 6.5 hours, filtered, washed with methanol and air dried. Approximately 55 grams of 2-(p-nitrophenyl)-5-nitrobenzoxazole are obtained.

The 2-(p-nitrophenyl)-5-nitrobenzoxazole is dissolved in 500 milliliters of 1,4-dioxane. A 10% palladium-on-carbon catalyst (2.0 grams) is added and the mixture heated to 70° C. Hydrogen gas is then bubbled into the solution until liquid chromatography shows that the reduction of the nitro groups is completed. The solvent is then evaporated and the resulting product is recrystallized from ethanol. About 37.5 grams of 2-(aminophenyl)-5-aminobenzoxazole is obtained.

EXAMPLE 2

Into 500 milliliters of ethanol are dissolved 75.5 grams (0.5 mole) of 4-nitrobenzaldehyde and 38 grams (0.55 mole) of hydroxylamine hydrochloride. The solution is heated at reflux for three hours, then poured into water, filtered and dried. Seventy-nine grams of 4-nitrobenzaldoxime is recovered.

Twenty-five grams (0.15 moles) of the 4-nitrobenzaldoxime is combined with 200 milliliters of 1,4-dioxane and 200 milliliters of concentrated HCl. The mixture is cooled to 10° C. and then 234 grams of a 5.25% aqueous solution of sodium hypochlorite (0.165 moles) are added dropwise, keeping the temperature of the mixture at about 10° C. Then, 200 milliliters of ice water are added, and the resulting mixture filtered, washed with more ice water, and dried. Twenty-four grams of 4-nitrophenylchloroxime (4-nitrophenyl hydroxamoyl chloride) are obtained.

To 10 grams (0.05 mole) of 4-nitrophenylchloroxime are added 150 milliliters of ethanol and a catalytic amount of 4-(N,N-dimethyl)aminopyridine. 4.0 grams of 2-amino-4-nitrophenol are added to the mixture. The mixture is stirred under nitrogen at room temperature for ninety minutes, at which time another 3.7 grams of 1-amino-4-nitrophenol are added. The mixture is then stirred overnight at room temperature under a nitrogen blanket, cooled to 20° C. and filtered to yield 2-(p-nitrophenyl)-5-nitrobenzoxazole.

A 7.5-gram portion of the 2-(p-nitrophenyl)-5-nitrobenzoxazole is dissolved in 100 milliliters of 1,4-dioxane. A 10% palladium-on-carbon catalyst (2.0 grams) is added, and the mixture stirred under nitrogen. The mixture is heated to 53° C., and hydrogen gas is bubbled into the mixture for about 6.5 hours. The catalyst is then filtered off and the remaining solution added to water. The solvent and water are then evaporated off to yield 2-(p-aminophenyl)-5-aminobenzoxazole.

EXAMPLE 3

Using the general procedure described in Example 2, except that 3-nitrobenzaldehyde is used in replace of the 4-benzaldehyde, 3-nitrobenzaldoxime is prepared.

A 4.98-gram (0.03 mole) portion of the 3-nitrobenzaldoxime is combined with 100 milliliters of 1,4-dioxane and 40 milliliters of concentrated HCl. The mixture is cooled to below 5° C. and then 47 grams of a 5.25% aqueous solution of sodium hypochlorite (0.033 mole) are added dropwise, keeping the temperature of the mixture at about 10° C. Then, 50 milliliters of ice water are added, and the resulting mixture is filtered, washed with more ice water, and dried to produce 3-nitrophenylchloroxime ( 3-nitrophenyl hydroxamoyl chloride).

To 11.5 grams (0.05 mole) of 3-nitrophenylchloroxime are added 150 milliliters of ethanol. To the mixture are added 23.1 grams (0.15 moles) of 2-amino-4-nitrophenol. The mixture is stirred under nitrogen at about 30° C. overnight and filtered to yield 2-(m-nitrophenyl)-5-nitrobenzoxazole.

A 11.1-gram portion of the 2-(m-nitrophenyl)-5-nitrobenzoxazole is dissolved in 200 milliliters of n-propanol. A 10% palladium-on-carbon catalyst (2.0 grams) is added, and the mixture stirred under nitrogen. The mixture is heated to 70° C., and hydrogen gas is bubbled into the mixture until substantially all the nitro groups have been reduced to primary amine groups, as indicated by liquid chromatography. The catalyst is then filtered off and the remaining solution added to water. The solvent and water are then evaporated off to yield 2-(m-aminophenyl)-5-aminobenzoxazole.

What is claimed is:

1. A process for preparing a 2-(aryl)-benz(ox, thi, imid)azole, comprising:
   (a) contacting an aromatic aldehyde with hydroxylamine under conditions such that an aromatic aldehyde oxime is formed;
   (b) contacting said aromatic aldehyde oxime under aqueous conditions with hypochlorous acid formed in situ from a mixture of HCl and a peroxysulfate salt or a mixture of sodium hypochlorite and a protic acid such that an aromatic hydroxamoyl halide is formed; and
   (c) contacting the aromatic hydroxamoyl halide with an aromatic amine compound which has a primary amine group ortho to a hydroxyl group, a thiol group or another primary amine group to form a 2-(aryl)-benz(ox, thi, imid)azole.

2. The process of claim 1 wherein neither the aromatic aldehyde nor the aromatic amine compound contains a nitro group, and the process further comprises the steps of contacting the 2-(aryl)-benz(ox, thi, imid)azole with a nitrating agent under conditions sufficient to add a nitro group to each of the aromatic ring structures, and then reducing the nitro groups to primary amine groups.

3. The process of claim 2 wherein the aromatic aldehyde has a —CHO group bonded to a pyridinyl, phenyl, anthracyl or naphthyl group.

4. The process of claim 3 wherein the aromatic amine compound is o-aminophenol.

5. The process of claim 1 wherein the aromatic aldehyde is nitro-substituted on an aromatic nucleus.

6. The process of claim 5 wherein the aromatic amine compound is not nitro-substituted and a 2-(nitroaryl)-benz(ox, thi, imid)azole is formed, and wherein the process further comprises the steps of contacting the 2-(nitroaryl)-benz(ox, thi, imid)azole with a nitrating agent under conditions sufficient to add a nitro group to the aromatic ring structure fused to the (ox, thi, imid)azole ring, and then reducing the nitro groups to primary amine groups.

7. The process of claim 6 wherein the aromatic aldehyde has a —CHO group bonded to a nitrophenyl, nitroanthracyl or nitronaphthyl group.

8. The process of claim 7 wherein the aromatic amine compound is o-aminophenol.

9. The process of claim 6 wherein the aromatic amine compound is nitro-substituted on an aromatic nucleus and a 2-(nitroaryl)-nitrobenz(ox, (thi, imid)azole is formed, and wherein the process further comprises reducing the nitro groups to primary amine groups.

10. The process of claim 9 wherein the aromatic aldehyde has a —CHO group bonded to a nitrophenyl, nitroanthracyl or nitronaphthyl group.

11. The process of claim 10 wherein the aromatic amine compound is 2-amino-4-nitrophenol.

* * * * *

UNITED STATES PATENT AND TRADEMARK OFFICE
CERTIFICATE OF CORRECTION

PATENT NO. : 5,567,843
DATED : October 22, 1996
INVENTOR(S) : Zenon Lysenko

It is certified that error appears in the above-identified patent and that said Letters Patent is hereby corrected as shown below:

Claim 9, column 8, line 21, "6" should correctly read - -5 - -

Signed and Sealed this

Twelfth Day of January, 1999

Attest:

Attesting Officer

*Acting Commissioner of Patents and Trademarks*